United States Patent [19]

Cvetovich et al.

[11] 4,360,684
[45] Nov. 23, 1982

[54] PROCESS FOR THE PREPARATION OF (2S)-TETRAHYDRO-2α-METHYL-6-OXO-4β-AMINO-2H-PYRAN-3α-CARBOXYLIC ACID

[75] Inventors: Raymond J. Cvetovich, Roselle Park; David G. Melillo, Scotch Plains; Kenneth M. Ryan, Clark; Meyer Sletzinger, North Plainfield, all of N.J.

[73] Assignee: Merck & Co., Inc., Rahway, N.J.

[21] Appl. No.: 252,492

[22] Filed: Apr. 8, 1981

[51] Int. Cl.³ .................................. C07D 309/30
[52] U.S. Cl. ...................... 549/291; 260/245.2 T; 260/239 A; 548/453; 560/171
[58] Field of Search ........................ 260/343.5

[56] References Cited

U.S. PATENT DOCUMENTS

| | | | |
|---|---|---|---|
| 4,269,772 | 5/1981 | Melillo et al. | 260/343.5 |
| 4,282,148 | 8/1981 | Liu et al. | 260/343.5 |
| 4,287,123 | 9/1981 | Liu et al. | 260/343.5 |

*Primary Examiner*—Jane T. Fan
*Attorney, Agent, or Firm*—Hesna J. Pfeiffer; James A. Arno

[57] ABSTRACT

Disclosed is a process for preparing (2S)-tetrahydro-2α-methyl-6-oxo-4β-amino-2H-pyran-3α-carboxylic acid (I) which is useful in the synthesis of thienamycin. The process proceeds via a stereospecific reduction of the 2-acetyl-3-(R)-α-methylbenzylamino-2-pentenedioic acid diester (II).

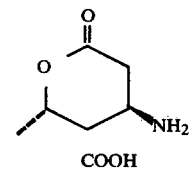

I

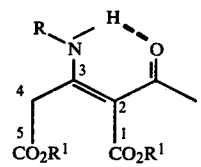

II wherein R is, α-methylbenzyl, and $R^1$ is lower alkyl having 1–6 carbon atoms or arylalkyl such as benzyl.

2 Claims, No Drawings

PROCESS FOR THE PREPARATION OF (2S)-TETRAHYDRO-2α-METHYL-6-OXO-4β-AMINO-2H-PYRAN-3α-CARBOXYLIC ACID

BACKGROUND OF THE INVENTION

This invention relates to the chiral synthesis of (2S)-tetrahydro-2α-methyl-6-oxo-4β-amino-2H-pyran-3α-carboxylic acid (I) which is useful in the synthesis of thienamycin (III).

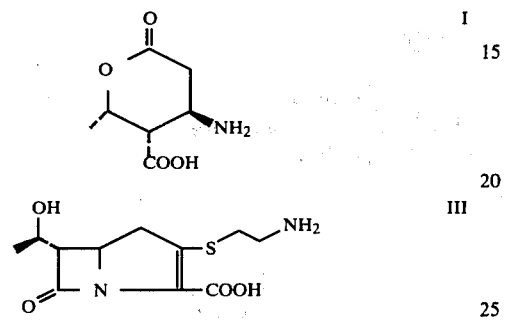

The total, stereo-controlled synthesis of thienamycin via lactone I has previously been described in co-pending commonly assigned U.S. Patent Application Ser. No. 112,020 Filed Jan. 14, 1980. However, this prior procedure produced I in a racemic state which required resolution, a step which resulted in a more than 50% loss in overall yield because the previous procedure produced 50% of the wrong enantiomer, which of course had to be discarded. The process of the present invention avoids the formation of the wrong enantiomer and hence is potentially higher-yielding and more economical.

The process of the present invention proceeds via the stereoselective reduction of a 2-acetyl-3-substituted amino-2-pentenedioic-acid diester (II).

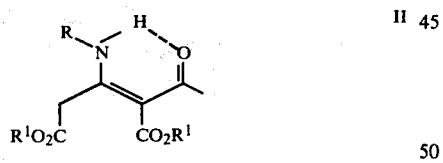

wherein R is (R)-α-methylbenzyl, or (S)-α-methylbenzyl, or esters of (R)- and (S)-α-carboxybenzyl, for example: —CH(C$_6$H$_5$)CO$_2$R$^n$ wherein R$^n$ is alkyl having 1-6 carbon atoms or aralkyl, such as methyl, ethyl, benzyl and the like. The R$^1$ ester moieties may be the same or different and are typically lower alkyl having from one to six carbon atoms such as methyl, ethyl, isopropyl, or the like, phenyl, or arylalkyl such as benzyl. The nature of the stereospecific reduction of (II) to give (I) to give thienamycin is discussed below.

DETAILED DESCRIPTION OF THE INVENTION

The process of the present invention may conveniently be summarized by the following reaction diagram:

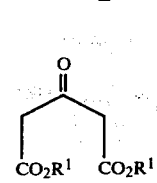
1

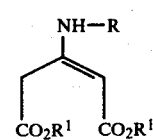
2

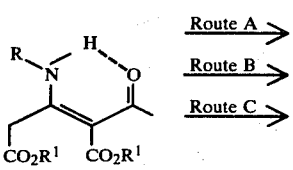
3

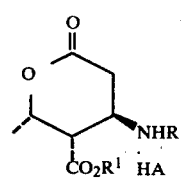
4

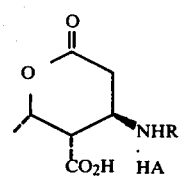
5

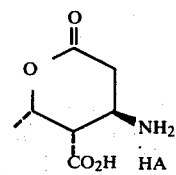
6

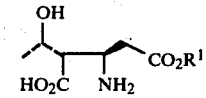
23

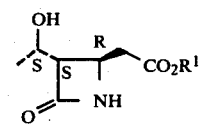
24

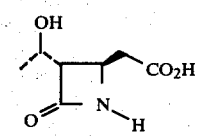
37

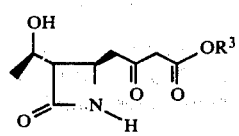
38

-continued

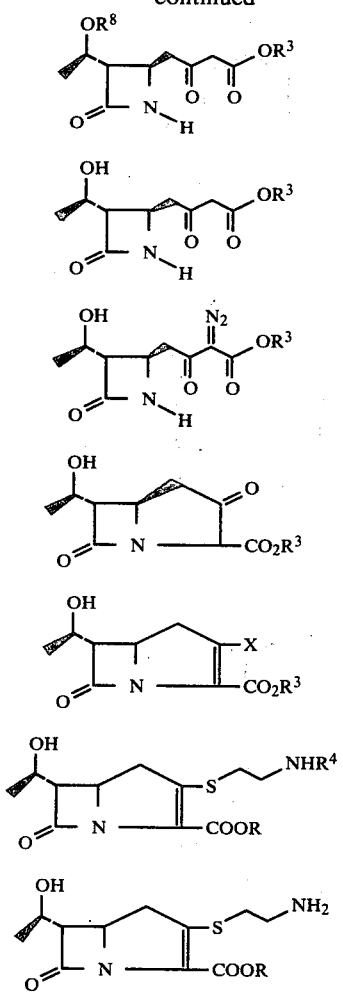

In words relative to the above reaction diagram, the acetonedicarboxylate starting material 1 ($R^1$ is alkyl having from 1–6 carbon atoms, aryl, such as phenyl, arylalkyl having from 7–12 carbon atoms) in a solvent such as toluene, methylene chloride, ethyl acetate, ether or the like is treated with an amine, $NH_2R$ (R is a catalytically removable, chiral arylalkyl group such as S-α-methylbenzyl, chiral esters of α-carboxybenzyl derived from α-phenylglycine, and preferably (R)-α-methylbenzyl) at a temperature of from −10° to 110° C. for from 0.5 to 24 hours. The above reaction mixture for the transformation 1 to 2 is conducted preferably in the presence of a dehydrating agent such as sodium sulfate, molecular sieves, or the like.

The transformation 2 to 3 is accomplished by treating 2 in a solvent such as toluene, methylene chloride, ethyl acetate, ether or the like with a stoichiometric to 100-fold excess of ketene, acetic anhydride, or acetyl halide such as acetyl chloride in the presence of a base such as a triorganoamine, for example, triethylamine, at a temperature of from −10° to 95° C. for from 10 minutes to 15 hours.

The transformation 3 to 4 may be accomplished by either Route A, Route B, or Route C. The following diagram summarizes these three routes:

ROUTE A

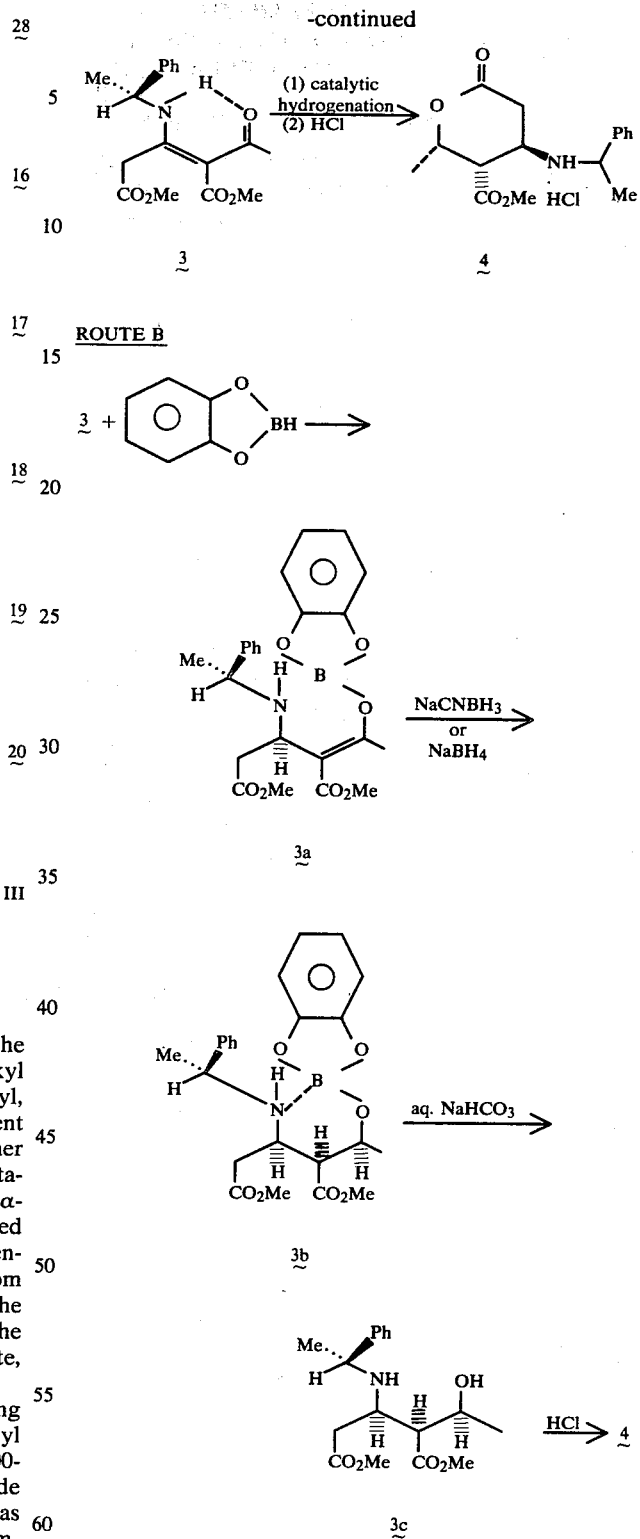

ROUTE C

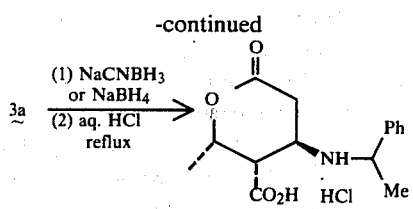

Route A. Typically the hydrogenation is conducted in the presence of a catalyst such as $PtO_2$ (preferably), Pd/C, Pt/C, Raney nickel, or the like, in a solvent such as isopropyl alcohol, methanol, ether, ethyl acetate, toluene, or the like, at a temperature of 0° to 85° C. for from 2 to 72 hours at a hydrogen pressure of from 1 to 100 atmospheres, preferably in the presence of an activating Lewis acid such as $BF_3.OEt_2$, $FeCl_3$, $AlCl_3$, or the like. Alternatively, the hydrogenation is conducted in the presence of a catalyst such as $PtO_2$ in a solvent like glacial acetic acid in the presence of a small amount of catalyst modifier such as $FeCl_3$, $SnCl_2$, $CoCl_2$ and the like which favors the reduction of the keto-enamine moiety relative to hydrogenation of the aromatic ring and in the presence of a strong acid like glacial acetic acid, tartaric acid, oxalic acid, hydrogen chloride, or trifluoroacetic acid, which activates the keto-enamine system towards reduction.

Route B is accomplished by treating 3 with a borane such as diborane, 9-borabicyclo[3.3.1]nonane, dibenzoyloxyborane, monochloroborane, dichloroborane, or preferably catecholborane. Typically the transformation 3 to 3a is accomplished in a solvent such as tetrahydrofuran, glyme, chloroform, toluene, or the like at a temperature of −100° to 80° C. for from 1 to 5 hours. The transformation 3a to 3b is accomplished by treating 3a in a solvent such as tetrahydrofuran, ether, acetic acid, chloroform, or the like with a reducing agent such as sodium cyanoboronhydride, sodium borohydride, conventional sodium acyloxyborohydrides, or the like in the presence of an acid such as acetic acid, propionic acid, oxalic acid, hydrochloric acid or the like.

The conversion of 3b to 3c is accomplished by solvolysis in $H_2O$, MeOH, or the like in the presence of a base such as sodium hydrogen carbonate, sodium carbonate, sodium hydroxide or the like at a temperature of from 0° to 40° C. for from 1 to 120 minutes.

The conversion of 3c to 4 is accomplished by treatment with an acid HA which may be sulfuric, acetic, hydrochloric or the like in a solvent such as $CH_2Cl_2$, toluene, ether, or the like at a temperature of from 20° to 50°.

The conversion of 3b to 4 (Route B') is accomplished with acids as described above in the presence of a small amount of protic material such as methanol, water, or the like in a solvent such as $CH_2Cl_2$, ether, or the like.

The transformation 4 to 5 is accomplished by treating 4 in water with a strong acid, such as p-toluenesulfonic acid, hydrochloric, or the like at a temperature from 25° to 120° C. for from 30 to 180 minutes to obtain free acid 5. Route C demonstrates schematically the continuity of the scheme in going from 3a to 5.

The amino deblocking transformation 5 to 6 is typically achieved by catalytic hydrogenation in a solvent such as acetic acid, water or the like under a hydrogen pressure of from 40–1500 psi in the presence of a hydrogenation catalyst such as palladium on charcoal, palladium oxide, platinum oxide or the like.

The transformation 6 to 23 is accomplished by treating 22 with an alcohol such as benzyl alcohol, phenol, 2,2,2-trichloroethanol, methanol, or the like at a temperature of from 25° to 100° C. for from 1 to 24 hours. In the representation of desired product 23 in the above diagram, the ester moiety $R^1$ is determined by the identity from the alcohol, $R^1OH$, used in the transformation 22 to 23. Suitable values for $R^1$ have been generically defined above relative to starting material 1; for purposes of definition $R^1$ embraces the definitions of $R^3$, also given above.

The transformation 23 to 24 is accomplished by treating 23 with dicyclohexylcarbodiimide (DCC), or the like in the presence of a base such as triethylamine, 4-dimethylaminopyridine, pyridine or the like.

The deblocking of the carboxyl group is accomplished in the transformation 24 to 37. Typically the deprotection is accomplished by catalytic hydrogenation. Typically, 24 and the solvent such as methanol, ethyl acetate, ether, or the like under a hydrogen pressure of from 1 to 3 atmospheres in the presence of a hydrogenation catalyst such as palladium on charcoal, platinum oxide, or the like is held at a temperature of from 0° to 40° C. for from 1 to 3 hours, to provide 37. Other deblocking procedures, such as hydrolysis, are also appropriate. Thus, for example, when $R^1$ is methyl, basic hydrolysis is preferred: Typically, this is accomplished by the addition of an equivalent amount of a base such as NaOH, KOH, $Ba(OH)_2$, $Na_2CO_3$, or the like to an aqueous solution of 24 (for example, as the methyl ester) at 25°–100° C. for from 10 minutes to 10 hours.

The addition 37 to 38 is accomplished by treating 37 with 1,1'-carbonyldiimidazole or the like in a solvent such as tetrahydrofuran, dimethoxyethane, or the like at a temperature of from 0° to 50° C., followed by the addition of 1.1 to 3.0 equivalents of $(R^3O_2CCH_2CO_2)_2Mg$, or the like, at a temperature of from 0° to 50° C. for from 1 to 48 hours. $R^3$ is readily removable carboxyl protecting group such as p-ntitrobenzyl, o-nitrobenzyl, benzyl or the like.

The transformation 38 to 28 is accomplished by treating 38 with a triorganophosphine in the co-presence of an activating agent therefor such as an azodicarboxylate, keto malonate, or the like to yield the intermediate phosphonium of 38 which is then reacted with an equivalent to 20-fold excess of a carboxylic acid such as formic, acetic, benzoic, or the like. Typically, the azodicarboxylate or its equivalent is added to the solution comprising the β-lactam substrate, the triorganophosphine and the carboxylic acid of choice, $R^8CO_2H$. The reaction is typically conducted in a solvent such as toluene, ethyl acetate, ether, methylene chloride or the like at a temperature of from −10° to 50° C. for from 10 minutes to 12 hours. Suitable triorganophosphines are triphenylphosphine, and trialkylphosphines, wherein the alkyl group has from 1–6 carbon atoms, for example, tributylphosphine. Suitable activating agents include, for example, azodicarboxylates such as diethylazodicarboxylate, dibenzylazodicarboxylate and diisopropylazodicarboxylate; diloweralkyl keto malonates wherein the alkyl moiety has from 1–6 carbon atoms are also suitable. Also effective to achieve the desired inversion is triphenylphosphine oxide and trifluoromethanesulfonic anhydride.

The transformation 28 to 16 is accomplished by treating 28 in a solvent such as methanol, ethanol or the like in the presence of an acid such as HCl, H₂SO₄, or a base such as sodium acetate or the like at a temperature of −10° to 28° C. for from 10 minutes to 12 hours.

The transformation 16 to 17 is accomplished by treating 16 in a solvent such as ethyl acetate, methylene chloride, toluene, or the like, with a diazotization reagent such as p-toluenesulfonyl azide, p-carboxybenzenesulfonyl azide or the like in the presence of a base such as pyridine, triethylamine, or the like at a temperature of from 0° to 40° C. for from 10 to 120 minutes.

Cyclization (17 to 18) is accomplished by treating 17 in a solvent such as benzene, toluene, THF or the like at a temperature of from 50°–100° C. for from 1–5 hours in the presence of a catalyst such as bis(acetylacetonato)-Cu(II) [Cu(acac)₂].CuSO₄, Cu powder, Rh₂(OAc)₄, or Pd(OAc)₂. Alternatively, the cyclization may be accomplished by irradiating 17 through a pyrex filter (a wave length greater than 300 nm) in a solvent such as benzene, CCl₄ diethylether or the like at a temperature of from 0°–25° C. for from 0.5 to 2 hours. ["OAc"=acetate].

Establishment of leaving group X (18 to 19) is accomplished by reacting the keto ester 18 with R⁰X such as p-toluenesulfonic acid anhydride, p-nitrophenylsulfonic acid anhydride, 2,4,6-triisopropylphenylsulfonic acid anhydride, methanesulfonic acid anhydride, p-toluenesulfonyl chloride, p-bromophenylsulfonyl chloride, or the like; wherein: X is the corresponding leaving group such as toluene sulfonyloxy, p-nitrophenylsulfonyloxy, methanesulfonyloxy, p-bromophenylsulfonyloxy; or other leaving groups which are established by conventional procedures and are well known in the art. Typically, the above reaction to establish leaving groups X is conducted in a solvent such as methylene chloride, acetonitrile or dimethylformamide, in the presence of a base such as diisopropylethylamine, triethylamine, 4-dimethylaminopyridine or the like at a temperature of from −20° to 40° C. for from 0.5 to 5 hours. The leaving group X of intermediate 19 can also be halogen. The halogen leaving group is established by treating 18 with a halogenating agent such as φ₃PCl₂, φ₃PBr₂, (φO)₃PBr₂, oxalyl chloride or the like in a solvent such as CH₂Cl₂, CH₃CN, THF, or the like in the presence of a base such as diisopropylethylamine, triethylamine, or 4-dimethylaminopyridine or the like. [φ=phenyl.]

The leaving group X can also be a phosphate. It is typically prepared by treating 18 with diethyl chlorophosphate or the like in the presence of a base such as diisopropylethylamine, triethylamine, or 4-dimethylaminopyridine or the like.

The leaving group X can also be a carbonate. It is preferred by treating 18 with a chloroformate such as methyl, benzyl, p-nitrobenzyl or the like in the presence of a base such as diisopropylethylamine, triethylamine, or 4-dimethylaminopyridine or the like.

The leaving group X can also be an imino ester:

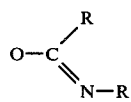

It is prepared by treating 18 with an imidoyl chloride such as N-phenyl trimethylacetimido chloride in the presence of a base such as diisopropylethylamine, triethylamine, or 4-dimethylaminopyridine or the like.

The reaction 19 to 20 is accomplished by treating 19 in a solvent such as dioxane, dimethylformamide, dimethylsulfoxide, acetonitrile, hexamethylphosphoramide, or the like in the presence of an approximately equivalent to excess of the mercaptan reagent HSCH₂CH₂NHR⁴ where R⁴ is hydrogen or a readily removable N-protecting group such as p-nitrobenzyloxycarbonyl, o-nitrobenzyloxycarbonyl, formimidoyl, phenoxyacetyl, phenylacetyl, 2-methyl-2-(o-nitrophenoxy)propionic, and o-nitrophenoxyacetic, or the like in the presence of a base such as sodium hydrogen carbonate, potassium carbonate, triethylamine, diisopropylethylamine, or the like at a temperature of from −40° to 25° C. for from 1 to 72 hours. The mercaptan reagent, HSCH₂CH₂NHR⁴, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours.

The final deblocking step 20 to III is accomplished by conventional procedures such as hydrolysis or hydrogenation, or enzymatically. Typically 20 in a solvent such as dioxane-water-ethanol; tetrahydrofuran-aqueous dipotassium hydrogen phosphate-isopropanol; tetrahydrofuran-water-morpholinopropane-sulfonic acid (adjusted pH to 7.0 by adding sodium hydroxide); or the like is treated under a hydrogen pressure of from 1 to 4 atmospheres in the presence of a hydrogenation catalyst such as palladium on charcoal, palladium hydroxide, platinum oxide, or the like at a temperature of from 0° to 50° C. for from 0.5 to 4 hours to provide III.

In the foregoing word description of the above schematic reaction diagram for the total synthesis of thienamycin, it is to be understood that there is considerable latitude in selection of precise reaction parameters. Suggestion of this latitude and its breadth is generally indicated by the enumeration of equivalent solvent system, temperature ranges, protecting groups, and range of identities of involved reagents. Further, it is, to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and thatcerain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation. All temperatures are in °C.

EXAMPLE 1

3(R)-α-methylbenzylamino-2-pentenedioic acid dimethyl ester

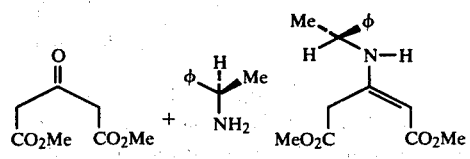

A mixture of (+)-α-phenethylamine (29.1 g, 0.24 mole), dimethyl 1,3-acetonedicarboxylate (41.9 g, 0.24 mole), and powdered 5A molecular sieves (84 g) in 100 ml Et₂O is stirred at room temperature for 16 hours. The suspension is filtered and the cake washed with a couple portions of Et₂O. The filtrate is concentrated to give the enamine as a white solid (67.5 g) which is used directly in the next reaction.

EXAMPLE 2

2-Acetyl-3-(R)-α-methylbenzylamino-2-pentenedioic acid dimethyl ester

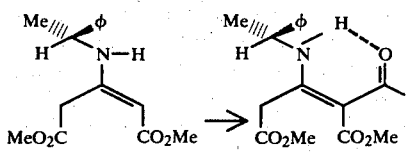

Ketene gas (generated by pyrolysis of acetone) is passed through a stirred solution of the enamine (65.7 g) in 1300 ml CH₂Cl₂ at room temperature. When starting material is completely consumed (followed by TLC on silica gel plates-solvent system 6/4, hexane/EtOAc) the solution is concentrated to give the product as an orange gummy solid (77.1 g).

The product may be recrystallized from 1 liter of cold 40% aqueous methanol to give the keto enamine as pink needles, m.p. 41.5°–43.5°. Washing with hexane gives the pure keto enamine, m.p. 47°–48°. $[\alpha]_D^{25} = -242$ (1% in MeOH).

EXAMPLE 3

(2S)-tetrahydro-2α-methyl-6-oxo-4β-[(R)-α-methylbenzylamino]-2H-pyran-3α-carboxylic acid methyl ester hydrochloride

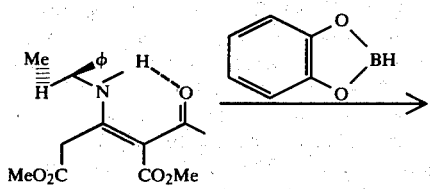

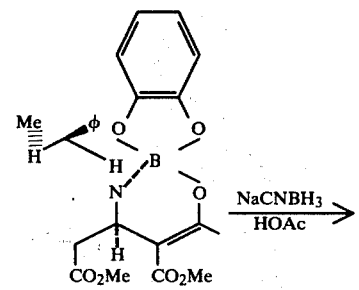

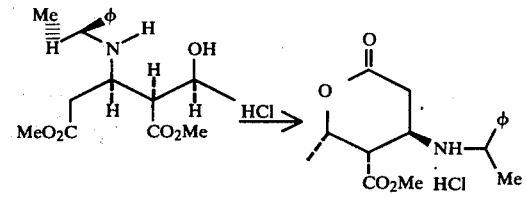

A solution of catecholborane (1.32 g, 11.0 mmoles) in 22 ml of anhydrous tetrahydrofuran (THF) is added dropwise over 13 minutes to a solution of the keto enamine (3.19 g, 10.0 mmoles) in 10 ml THF at −78° C. The resulting solution is aged at −78° for 2.5 hours and then concentrated to a mobile oil (at this point a small amount of the THF remains to give the crude product the mobility). This oil is rapidly dissolved in 10 ml glacial acetic acid (HOAc), chilled to about 10° in an ice-bath, and treated rapidly with a solution of NaCNBH₃ (628 mg, 10.0 mmoles) in 11 ml HOAc. The resulting solution is aged at room temperature for 1.5 hours and then concentrated in vacuo. The residue is partitioned between ethyl acetate (EtOAc) and two portions of saturated aqueous NaHCO₃. The aqueous extracts are back-extracted with EtOAc. The combined organic layers are washed with brine, dried with Na₂SO₄, and concentrated in vacuo to give the amino alcohol as a yellow oil (4.05 g). This oil is dissolved in 35 ml CH₂Cl₂ and 35 ml Et₂O, chilled to 0°, and saturated with HCl gas. The solid that crystallizes is filtered, washed with three portions of cold 40% CH₂Cl₂/Et₂O, and dried in vacuo to give the pure lactone ester (1.28 g, 39%) as a white powder, m.p.=186° (dec.).

The filtrate contains another 8% of the desired product (determined by HPLC assay-silica gel base, propylnaphthamide stationary phase, CHCl₃/MeCN solvent system).

EXAMPLE 4

(2S)-tetrahydro-2α-methyl-6-oxo-4β-[(R)-α-methylbenzylamino]-2H-pyran-3α-carboxylic acid methyl ester hydrochloride

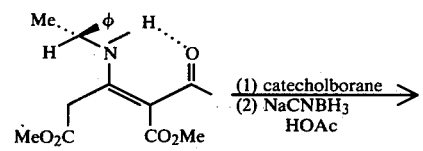

-continued

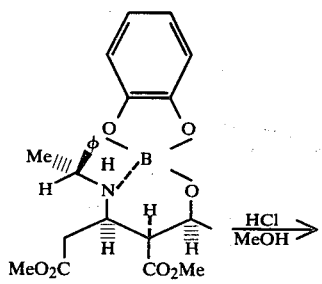

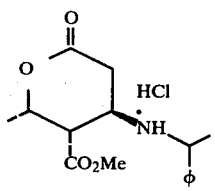

Alternative: Non-Aqueous Work-up

The borane and hydride reductions are conducted as described above. The acetic acid is removed in vacuo from the hydride reduction and replaced with 50% CH2Cl2/Et2O. The solution is saturated with HCl gas, a small amount of MeOH (approx. ½ ml) is added to help solvolyze the chelate, and aged at 0° for 15 hours. The solid is collected by filtration, washed with 60% Et2O/CH2Cl2, and dried in vacuo. The solid, which is contaminated with inorganic impurities but not organic material, can be used directly in the hydrolysis reaction.

EXAMPLE 5

(2S)-tetrahydro-2α-methyl-6-oxo-4β-[(R)-α-methylbenzylamino]-2H-pyran-3α-carboxylic acid hydrochloride

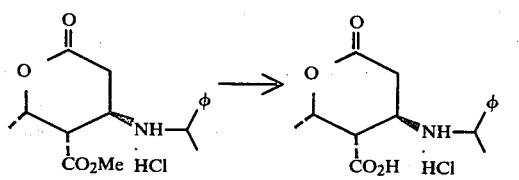

A suspension of the ester lactone (2.14 g, 6.53 mmole) in 10 ml of conc. aqueous HCl is heated to reflux for 2 hours. The resulting solution is cooled to 0° whereupon the acid crystallizes. After 1 hour, the solid is filtered, washed with Et2O, and dried in vacuo to give the pure acid, 1.386 g (68%), mp.=182° (dec.).

The filtrate can be concentrated in vacuo and the solid residue washed with several portions of Et2O to give an additional 0.47 g (23%) of product as a tan powder.

EXAMPLE 6

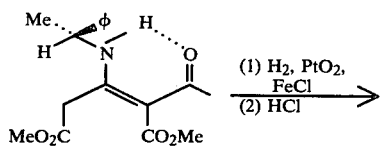

I. A solution of (R)-α-methyl keto-enamine 3 (0.638 g, 2.0 mmole) in 20 ml isopropanol is pressurized (150 psi) with hydrogen gas in the presence of PtO2 (0.1 g) and FeCl3 (0.342 g, 2.1 mmole) and shaken at room temperature for 20 hours. The suspension is filtered and the solid washed with 5 ml of IPA. The combined filtrates are concentrated to give a dark oil which is redissolved in 20 ml of EtOAc. This solution is treated with 0.25 ml concentrated NH4OH (aq) and stirred for 20 minutes. The resulting suspension is filtered through celite to give a clear colorless solution which is concentrated in vacuo to an oil and redissolved in 5 ml of methylene chloride. This solution is treated with anhydrous hydrogen chloride and the product is crystallized upon addition of 7 ml of ether.

II. A solution of (R)-α-methyl keto enamine 3 (0.638 g, 2.0 mmole) in 10 ml. glacial acetic acid is pressurized (40 psi) with hydrogen gas in the presence of PtO2 (0.1 g), FeCl3 (0.001 g) and trifluoroacetic acid (0.15 ml, 1.95 mmole) and shaken at room temperature for 6 hours. The suspension is filtered and the solid is washed with 5 ml HOAc. The combined filtrates are concentrated to give a yellow oil which is redissolved in 5 ml of methylene chloride. This solution is treated with anhydrous hydrogen chloride and the product is crystallized upon addition of 7 ml of ether.

EXAMPLE 7

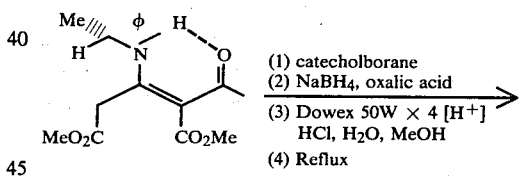

A solution of catecholborane (1.32 g, 11.0 mmoles) in 22 ml dry THF is added to a solution of keto enamine (3.19 g, 10.0 mmoles) in 10 ml THF at −78°. The solution is aged at −78° for 2 hours and then oxalic acid hydrate (12.6 g, 100 mmoles) in 47 ml EtOH is added followed immediately with a solution of NaBH4 (1.14 g, 30 mmoles) in 47 ml EtOH. The yellow suspension is allowed to warm to room temperature and aged overnight. The suspension is filtered and the filtrate is diluted with H2O (20 ml) and charged on a column of 30 ml of Dowex 50WX4 ion exchange resin (H+ cycle). The column is washed with 80% MeOH/H2O until the washes are oxalic acid free. The product is then eluted with 6 N HCl in 50% aqueous methanol (approximately 200 ml). The eluate is heated to reflux and low boilers are removed until the volume of the pot residue is 30 ml. After 3–4 hours of heating, the remainder of the solvent is removed in vacuo. The residue is washed with several portions of Et$_2$O to give the crude lactone acid as a white powder, 2.34 g. Pure acid is obtained as a white powder by stirring the crude material in CH$_2$Cl$_2$ overnight at room temperature.

EXAMPLE 8

(2S)-tetrahydro-2α-methyl-6-oxo-4β-amino-2H-pyran-3α-carboxylic acid hydrochloride

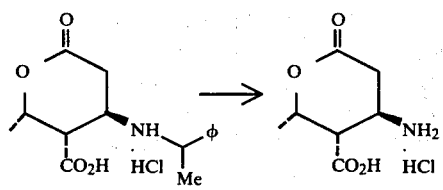

A suspension of the lactone acid (100 mg, 0.318 mmole) and 50 mg of 5% Pd/C in 3 ml HOAc is shaken under 100 psi H$_2$ for 3 days at room temperature. The suspension is filtered and the filtrate concentrated to give the primary amine as a colorless gum, 92 mg.

$[\alpha]_D^{25} = -50.5$ in 0.12 N aq. HCl

The 'H-NMR of this material was identical to that of a sample prepared by catalytic hydrogenolysis of a sample of racemic N-benzyl lactone.

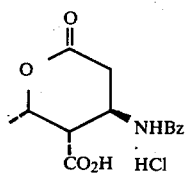

EXAMPLE 9

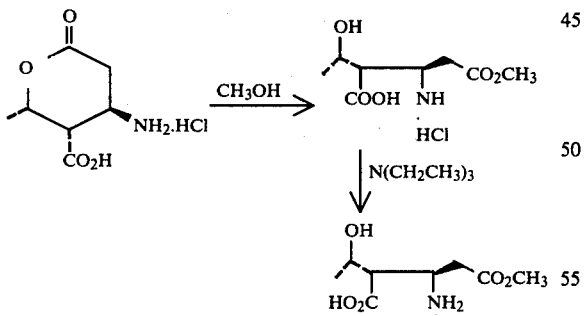

A solution of 4.78 moles of the lactone in 19 liters of methanol is refluxed for 3 hours. After aging at room temperature overnight, the solution is concentrated under vacuum. The oil is dissolved in 12 liters of methylene chloride and then treated with a solution of NEt$_3$ (710 ml, 5.02 moles) over 1 hour at room temperature. The mixture is stirred at room temperature for 10 hours. The product is collected by filtration, washed with two 4-liter portion of CH$_2$Cl$_2$ and air dried to give the amino acid as a white crystalline solid.

EXAMPLE 10

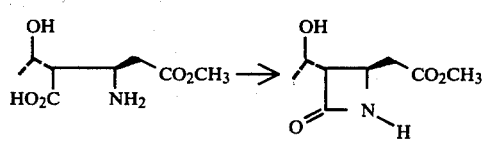

A suspension of the amino acid (20.0 g, 0.097 moles) in 400 ml MeCN is treated with a solution of N, N'-dicyclohexylcarbodiimide (21.0 g, 0.102 moles) in 100 ml MeCN followed by enough water (ca. 70 ml) to nearly achieve a homogeneous solution. The mixture is then heated to 30°–35° for 5 hours. The suspension is cooled to 0°–5°, filtered, and the filtrate concentrated in vacuo. The residue is dissolved in 150 ml CH$_2$Cl$_2$ and the product is extracted into three 50 ml portions of water. This aqueous solution may be used directly in the next step (saponification) or it may be concentrated in vacuo to give pure β-lactam (16.8 g, 92%).

EXAMPLE 11

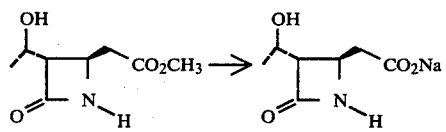

At room temperature, 1.05 moles of 6 N aqueous sodium hydroxide solution is added to a stirred solution of the methyl ester (23.6 g, 0.126 mole) in 70 ml H$_2$O. After aging at 25° for 1 hour, the pH of the solution is adjusted to 8.5 by addition of 2 N aqueous HCl and then most of the water is removed in vacuo. The residue is dissolved in 75 ml MeOH, isopropanol (175 ml) is then added and the suspension cooled to 0°–5° for 1 hour. The product is filtered and dried to constant weight in vacuo (21.4 g, 87%).

EXAMPLE 12

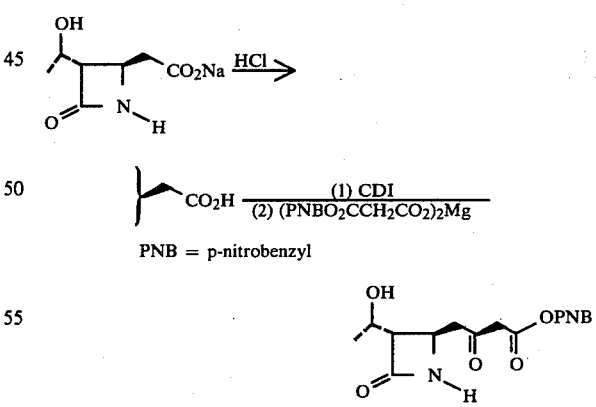

PNB = p-nitrobenzyl

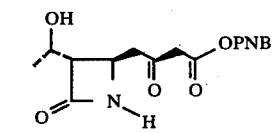

The sodium salt (10.0 g, 51.3 mmol) in 30 ml of dry dimethyl formamide is treated with 22.5 ml of 2.3 M HCl in DMF (51.7 mmol) to give a nearly homogeneous solution. After stirring at room temperature for an additional 10 minutes, the solution is diluted with 300 ml dry MeCN. The resulting mixture is stirred for 30 min. and then treated with N,N-carbonyldiimidazole (CDI: 8.29 g, 25.6 mmol), and aged for 20 hours. The solvent is removed in vacuo and the residue is partitioned between 200 ml 1 N aqueous HCl and two portions of CH₂Cl₂ (total volume 500 ml). The combined organic extracts are washed with dilute aqueous NaHCO₂, dried over Na₂SO₄, and concentrated in vacuo to give the β-keto ester as an oil (15.1 g, 84%).

EXAMPLE 12a

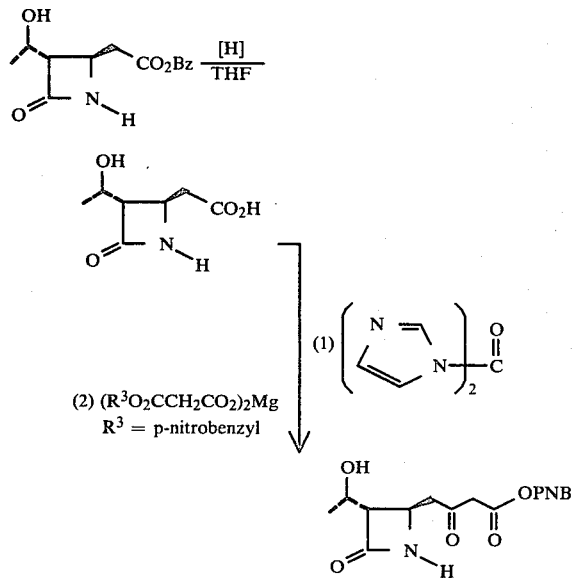

A mixture of the β-lactam (2.50 g, 9.49 mmoles) and 0.5 g of 10% Pd/C in 50 ml of tetrahydrofuran is hydrogenated at 40 psi on a Parr shaker for 2 hours. The suspension is filtered and to the filtrate is added 1,1'-carbonyldiimidazole (1.61 g, 9.93 mmoles) as a solid and the solution is aged at room temperature under a nitrogen atmosphere for 3 hours. To this solution is added the magnesium salt of p-nitrobenzyl hydrogen malonate (4.97 g, 9.93 mmole) and the resulting solution which soon becomes a suspension is stirred at room temperature for 20 hours. The suspension is concentrated in vacuo and the residue in CH₂Cl₂ is washed with dilute aqueous HCl followed by aqueous NaHCO₃. Each aqueous extract is back-washed with CH₂Cl₂. The combined organic layers are dried and concentrated in vacuo to give the product as a pale-yellow gum, 2.92 g. Pure material may be obtained as a gum by chromatography on silica gel and elution with EtOAc.

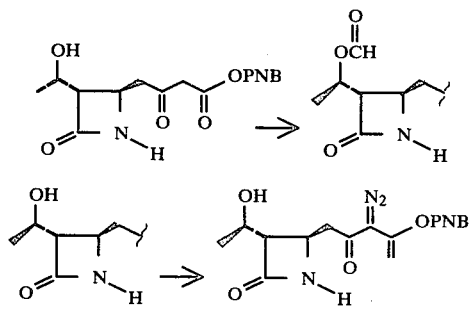

A solution of diisopropyl azodicarboxylate (139 mg, 0.69 mmole) in 1 ml of dry tetrahydrofuran is added dropwise to a stirred, chilled (ice-bath) solution of the β-lactam (130 mg, 0.37 mol), triphenylphosphine (181 mg, 0.69 mmole), and 95-100% formic acid (51 mg, 1.11 mmol) in 1.5 ml tetrahydrofuran. The solution is aged at 0° for 10 min. then at room temperature for 1 hour. The solution is concentrated, the residue is dissolved in 9 ml of aqueous MeOH, and treated with 0.4 ml conc. HCl. The mixture is aged at room temperature for 1.5 hours and then concentrated almost to dryness. The residue is partitioned between water and the two portions of CH₂Cl₂. The combined organic extracts are dried (MgSO₄) and concentrated to give a yellow gum (430 mg). A solution of this crude product and p-toluenesulfonyl azide (81 mg, 0.41 mmol) in 1 ml EtOAc at 0° is treated with a solution of triethylamine (41 mg, 0.41 mmol) in 0.5 ml EtOAc. The mixture is stirred at 0° and after 5-10 min. the diazo derivative begins to precipitate. After 45 min., the product is collected by filtration, washed with three portions of cold EtOAc, and dried to give the pure diazo keto ester (85 mg, 61% overall) as a pale-yellow powder, m.p. 150°-2° (dec.).

EXAMPLE 13

(3S, 4R)-α-diazo-3[1(R)-hydroxyethyl]-β,2-dioxo-4-azetidinebutanoic acid p-nitrobenzyl ester 15

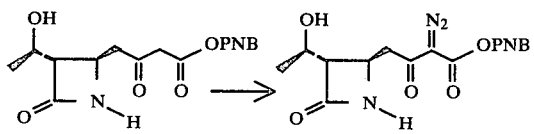

A solution of the crude β-keto ester 14 (0.83 g, 2.37 mmole) and p-toluenesulfonyl azide (0.56 g, 2.85 mmole) in 10 ml EtOAc at room temperature is treated with a solution of NEt₃ (0.31 g, 3.08 mmole) in 2 ml EtOAc. The resulting suspension is stirred for 1 hr., chilled to 0° and filtered to yield pure product 15.

| Elem. Anal. | Calcd. | Found |
|---|---|---|
| C₁₆H₁₆N₄O₇ | 51.06 | 51.04 |
|  | 4.29 | 4.22 |
|  | 14.89 | 14.76 |

EXAMPLE 14

(5R, 6S)-6-[(R)-1-hydroxyethyl]-3,7-dioxo-1-azabicyclo[3.2.0]heptane-2-carboxylic acid p-nitrobenzyl ester

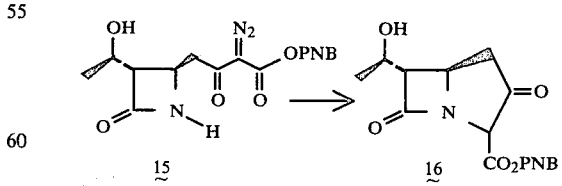

A stirred suspension of the diazo compound 15 (500 mg, 1.33 mmole) and rhodium diacetate (15 mg) in dry toluene (35 ml) is heated to 80°-5° for 2.5 hours. After filtration of the catalyst, the solution is concentrated in vacuo to give the product as a white solid, mp 92°-8°.

EXAMPLE 15

(5R,6S)-6-[(R)-1-hydroxyethyl]-3-[2-(p-nitrobenzyloxycarbonyl)aminoethylthio]-7-oxo-1-azabicyclo[3.2.0-]hept-2-enen-2-carboxylic acid p-nitrobenzyl ester

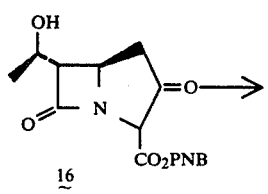

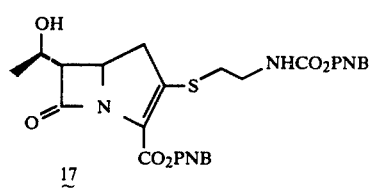

PROCEDURE A: Trifluoromethylsulfonyl Activation

To a stirred suspension of the bicyclic ketone 16 (100 mg, 0.287 mmole) in dry methylene chloride (1 ml) is added dropwise a solution of diisopropylethylamine (62 mg, 0.481 mmole) in dry CH$_2$Cl$_2$ (0.4 ml) at 0° under nitrogen atmosphere. The resulting mixture is aged for 15 min. then trifluoromethanesulfonic anhydride (90 mg, 0.319 mmole) is added to give a clear solution. To the mixture is added a solution of diisopropylethylamine (250 mg, 1.94 mmole) in CH$_2$Cl$_2$ (0.3 ml) followed by N-p-nitrobenzyloxycarbonylcysteamine (77 mg, 0.30 mmole) as a solid at 0° C. The mixture is stirred for 30 min. during which time the product crystallizes as a colorless solid. The solid is collected by filtration and washed with CH$_2$Cl$_2$. An additional crop of product is obtained by washing the filtrate with dilute aqueous NaHCO$_3$. The organic layer is dried with Na$_2$SO$_4$ and concentrated in vacuo. The residue is crystallized from EtOAC to provide pure product 17.

PROCEDURE B: Tosylate Activation

To a suspension of the bicyclic ketone 16 (50 mg, 0.144 mmole) in acetonitrile (3 ml) is added dropwise a solution of diisopropylethylamine (22 mg, 0.171 mmole) in 1 ml CH$_3$CN at −5° C. under a nitrogen atmosphere. After aging at this temperature for 10 min., a solution of p-toluenesulfonic anhydride (51 mg, 0.156 mmole) in 1 ml CH$_3$CN is added. The resulting mixture is stirred for 2 hr. at 0° C. The solution is concentrated in vacuo to a volume of approximately 1 ml and then 3 ml of dry, N,N-dimethylformamide (DMF) is added and the remaining CH$_3$CN removed in vacuo. To the DMF solution at −5° C. is added a solution of diisopropylethylamine (40 mg, 0.31 mmole) in 0.5 ml DMF followed by N-p-nitrobenzyloxycarbonylcysteamine (39 mg, 0.15 mmole) and the resulting mixture stored in a refrigerator for 70 hrs. The solution is diluted with brine and extracted with five portions of CH$_2$Cl$_2$. The combined extracts are washed with brine, dried over Na$_2$SO$_4$, and concentrated in vacuo. The residue is crystallized from an ethyl acetate-ether mixture to give pure product 17 as a colorless solid.

PROCEDURE C: Phosphate Activation

To a suspension of the bicyclic ketone 16 (100 mg, 0.29 mmole) in CH$_3$CN (1 ml) is added dropwise a solution of diisopropylethylamine (37 mg, 0.29 mmole) in 0.4 ml CH$_3$CN at 0° under a nitrogen atmosphere. The resulting mixture is stirred for 15 min. then a solution of diphenyl chlorophosphate (77 mg. 0.29 mmole) in 0.4 CH$_3$CN is added. The mixture is stirred for 15 min. at 0° and then 15 min. at room temperature. The mixture is again cooled to 0° and a solution of diisopropylethylamine (38.7 mg, 0.30 mmole) in 0.4 ml CH$_3$CN is added followed by N-p-nitrobenzyloxycarbonylcysteamine (77 mg, 0.30 mmole). The reaction mixture is stored overnight in a freezer, diluted with EtOAC, and filtered to give pure product 17 as a colorless solid.

EXAMPLE 6

Thienamycin

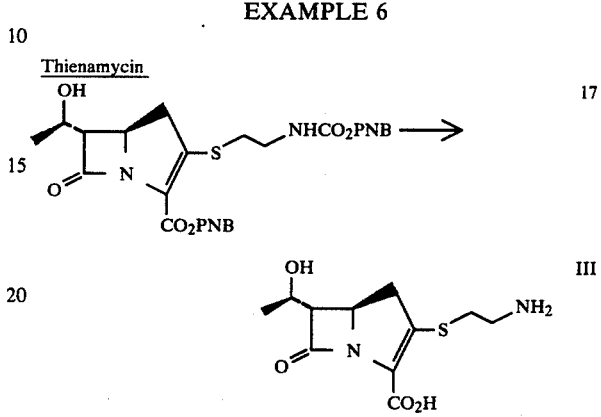

A mixture of the protected thienamycin 17 (4.9 mg, 8.362×10$^{-6}$ mole) and platinum oxide (3.4 mg) in tetrahydrofuran (2 ml), water (1 ml) and 0.5 M morpholinopropanesulfonic acid (adjusted to pH 7.0 by adding sodium hydroxide) (0.5 ml) is hydrogenated at 40 psi on a Parr shaker for 60 minutes. The suspension is filtered to remove catalyst and the catalyst is washed with water (2×20 ml). The filtrate is washed with EtOAC (2×15 ml) to provide pure thienamycin III.

What is claimed is:

1. A stereoselective reductive process for preparing

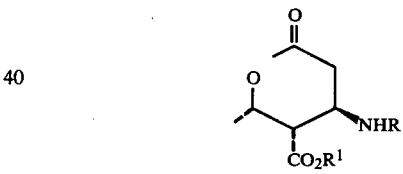

comprising reaction of

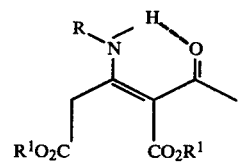

with 1-100 atmospheres pressure hydrogen gas, in the presence of a catalytic amount of PtO$_2$, Pd/C, Pt/C, or Raney nickel; in a solvent which is isopropyl alcohol, methanol, ether, ethyl acetate or toluene; at a temperature of 0°-85° C. for from 2-72 hours; and in the presence of an activating Lewis acid which is BF$_3$.OEt$_2$, FeCl$_3$ or AlCl$_3$; wherein R$^1$ is alkyl having 1-6 carbon atoms or benzyl;

and R is (R)-α-methyl benzyl or (S)-α-methylbenzyl or lower alkyl esters of (R)- and (S)-α-carboxybenzyl or benzyl esters of (R)-and (S)-α-carboxy-benzyl.

2. The process of claim 1 wherein R$^1$ is methyl and R is α-methyl benzyl.

* * * * *